United States Patent [19]

Kasha

[11] Patent Number: 4,731,458

[45] Date of Patent: Mar. 15, 1988

[54] SPIRO[BICYCLO[3.2.0]HEPTANE-6,2'-OXIRANE] DERIVATIVES

[75] Inventor: Walter J. Kasha, Los Angeles, Calif.

[73] Assignee: CBD Corporation, Los Angeles, Calif.

[21] Appl. No.: 855,720

[22] Filed: Apr. 25, 1986

[51] Int. Cl.$^4$ .................. C07D 303/22; C07D 303/16; C07D 303/40; C07D 407/08; C07F 7/18
[52] U.S. Cl. ..................................... 549/215; 549/332
[58] Field of Search ................................ 549/215, 332

Primary Examiner—Norma S. Milestone
Attorney, Agent, or Firm—Wegner & Bretschneider

[57] ABSTRACT

Compounds of the formula

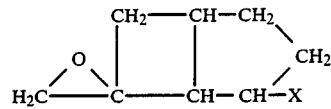

are described wherein X is a $C^{2-11}$-alkyl group, optionally substituted by a protected hydroxy, protected oxo or protected carboxy group.

9 Claims, No Drawings

SPIRO[BICYCLO[3.2.0]HEPTANE-6,2'-OXIRANE] DERIVATIVES

The present invention provides spiro[bicyclo[3.2.0]heptane-6,2'-oxirane] derivatives of the structural formula

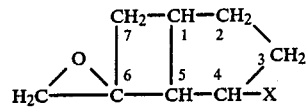 (I)

wherein X is a hydrocarbon group which is optionally substituted by a $C^{1-4}$-alkoxy group, a protected hydroxy, protected oxo or protected carboxy group.

The hydrocarbon radical serving as the 4-substituent preferably contains 2 to 11 carbon atoms. Especially preferred are straight-chain or branched alkyl groups. The hydrocarbon radical may also be an arylalkyl group such as phenethyl, tolylethyl, phenylpropyl, phenylbutyl or phenylpentyl. The hydrocarbon radical may also contain a $C^{3-6}$-cycloalkyl group.

The alkoxy group substituted on the X radical can be methoxy, ethoxy, straight-chain or branched propyl or butyl.

Conventional substituent groups can be used to protect a hydroxy, oxo, formyl or carboxyl group which may be attached to the X radical against reaction with a methylide reagent such as dimethylsulfonium methylide or dimethyloxosulfonium methylide.

The hydroxy group can be protected as $C^{1-4}$-alkoxy, $C^{6-9}$-aryloxy, $C^{1-5}$-alkanoyloxy, $C^{1-6}$-alkylsulfonyloxy, $C^{6-9}$-arylsulfonyloxy or as a silyl ether derivative, e.g. a tri($C^{1-5}$-alkyl)silyloxy or a corresponding phenyl alkyl silyloxy derivative.

The carboxyl group can be protected conveniently as a $C^{1-9}$-alkyl ester, $C^{6-9}$-arylalkyl ester and the like.

Aldehydic or oxo groups can be protected as conventional acetals or ketals.

The aryl moiety in the protecting group can be phenyl, tolyl, xylyl, cumyl and the like.

The spiro oxiranes of formula (I) are useful as intermediates for the preparation of substituted bicyclo[3.3.0]octan-7-ones of the formula

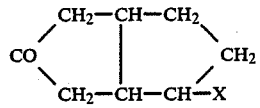 (II)

which have been described by Kasha and Burnison (Ser. No. 838,760, filed March 12, 1986, now U.S. Pat. No. 4,689,345) and which have valuable properties as anti-androgenic agents and are useful, i.a. in alleviation of acne, increasing elastin/collagen ratio, preventing keloids and controlling microorganisms having androgen receptor sites. In formula II, X' represents a hydrocarbon group and typically an alkyl group comparable to X in formula I, which is optionally substituted by a free hydroxy, free oxo, free carboxyl group or a protected group such as an etherified or esterified hydroxy group, or an esterified carboxyl group. The oxo group can be conventionally protected by an acetal or ketal group.

In the process of the application of Kasha and Burnison cited above, compounds of formula II are prepared as follows. A cyclopentene with a 3-X substituent

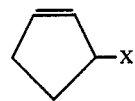

is reacted with dichloroacetyl or trichloroacetyl chloride to form, as the predominant isomer, a 4-X- or 4-X'-substituted 7,7-dichlorobicyclo[3.2.0]heptan-6-one. Such a compound

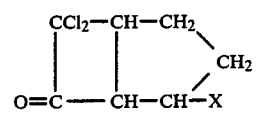 (III)

also serves as an intermediate in the present process. Kasha and Burnison then react the compound of formula III, substituted by X', at the 4-position with diazomethane to produce a ring enlargement to the compound of formula II. It is possible that this reaction proceeds by way of a 4-X'-substituted 7,7-dichloro spiro[bicyclo[3.2.0]heptane-6,2'-oxirane] derivative of very short life. The hazards of such diazomethane reaction are obvious, especially if the reaction is carried out on an industrial scale.

A relatively safe and effective process has now been found which avoids the use of diazomethane. A compound of formula III is first dehalogenated, e.g. by use of zinc and acetic acid, to form the 4-X substituted bicyclo[3.2.0]heptan-6-one. In the following step, the 6-oxo group is reacted with an ylide reagent to form the spiro oxirane derivative. In order to avoid reactions of substituents on the X side chain, functional groups such as hydroxyl, oxo or carboxyl groups must be protected, so that this side chain in the 4-position does not react with an ylide reagent.

A preferred ylide reagent is dimethylsulfonium methylide. Also useful are other methylides such as dimethyloxosulfonium methylide.

The reaction is conveniently carried out in an inert atmosphere, by adding to a solution of the methylide in a solvent such as dimethylsulfoxide. To this solution is added the 4-X substituted bicyclo[3.2.0]heptan-6-one of the formula

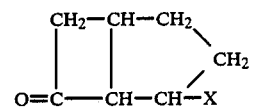 (IV)

The reaction is conveniently carried out by heating, e.g. at about 40° C. for an hour, to yield the 4-X substituted spiro[bicyclo[3.2.0]heptane-6,2'-oxirane], which is conveniently stored under refrigeration until needed for further use.

If kept in a warm room, e.g. at 30° C., for three days, the product rearranges to form the 4-X substituted bicyclo[3.2.0]heptan-7-ones, corresponding to formula II. This conversion is achieved more efficiently by mild heating with conventional reagents such as lithium iodide.

The spiro oxiranes of this invention can be used to produce anti-androgenic effects of the type produced by the compounds of the formula II. They produce the inhibitory effect on pathogenic agents such as Candida, Actinomyces, Norcardia and like pathogenic agent with androgen receptor sites. They are effective at concentrations of 1:1 to 1:1000.

Where free hydroxyl, carbonyl or carboxyl substituents are desired on group X' in the bicyclo[3.3.0]octan-7-ones of type II, the protective groups are removed by conventional methods.

EXAMPLE 1

4-(5-Methoxyheptyl)bicyclo[3.2.0]heptan-6-one

A. A three-neck, round-bottomed flask containing magnesium metal turnings (7.2 g, 0.299 moles), is equipped with a Friedrich condenser and kept under a nitrogen atmosphere. Tetrahydrofuran (300 ml) is added and the contents are allowed to stir. A solution of 1-chloro-5-methoxyheptane (48.1 g, 0.292 moles) is added in small portions and refluxed. The mixture is allowed to stir for 3 hours. The resultant dark yellow solution is cooled to −25° C., and the condenser is removed and replaced with a dry ice addition funnel. A solution of 3-chlorocyclopentene (29.9 g, 0.292 moles) is added over a period of one hour. The viscous solution is poured into two liters of saturated ammonium chloride, extracted with ether, and dried over anhydrous sodium sulfate. Distillation yields 3-(5-methoxyheptyl)cyclopentene (51.5 g, 0.262 moles) as a clear, colorless oil boiling at about 90° C. at 0.3 mm and 54° C. at 0.1 mm.

B. A 1,000 ml three-neck, round-bottomed flask, containing 3-(5-methoxyheptyl)cyclopentene (15.0 g, 0.076 moles) in 300 ml of hexane, is equipped with a reflux condenser. Freshly distilled dichloroacetyl chloride (35.1 g, 0.240 moles) is added and the solution stirred and heated to reflux. Triethylamine (25.2 g, 0.249 moles) in 200 ml hexane, is added dropwise to the refluxing solution and the solution allowed to stir for 4 hours. The solvent is removed and the residue distilled and chromatographically purified with silica gel, leaving the product (17 g) of the formula 7,7-dichloro-4-(5-methoxyheptyl)bicyclo [3.2.0]heptan-6-one (Formula III, $X=-(CH_2)_4-CH(OCH_3)-C_2H_5$).

Analysis: IR: 2963, 2932, 2864, 2857, 2820, 1803, 1461, 1378, 1223, 1197, 1157, 1093, 1030, 968, 914, 842,821, 802, 778, 740, and 673 cm$^{-1}$.

C. Zinc (4 g) is added to a stirred solution of 7,7-dichloro-4-(5-methoxyheptyl)bicyclo[3.2.0]heptan-6-one (2 g) in glacial acetic acid (120 ml). The solution is stirred at room temperature for one hour, then refluxed for 1 hour, after which time the mixture is filtered through a sintered glass funnel and the ether solution dried over anhydrous sodium sulfate. The solvent is removed under vacuum, leaving the crude product. Chromatography on silica gel yields 4-(5-methoxyheptyl)bicyclo [3.2.0]heptan-6-one (Formula IV, $X=-(CH_2)_4-CH(OCH_3)-C_2H_5$).

Analysis: IR: 2959, 2933, 2859, 2820, 1778, 1461, 1406, 1386, 1316, 1303, 1260, 1236, 1197, 1154, 1091, 1024, 921, and 819 cm$^{-1}$.

EXAMPLE 2

4-(5-Methoxyheptyl)spiro[bicyclo[3.2.0]heptane-6,2'-oxirane]

A 250 ml, 3-necked round bottomed flask is equipped with a magnetic stirrer. The reaction is conducted under a positive nitrogen pressure, maintained with an oil filled bubbler. The reaction vessel is charged with dimethyloxosulfonium methylide (36 ml of 0.932M solution, 0.034 moles) in dimethyl sulfoxide. 4-(5-Methoxyheptyl)bicyclo[3.2.0]heptan-6-one (7.7 g, 0.032 moles) is added neat to the stirring solution by a syringe. The reaction vessel is heated in a 40° C. water bath for 60 minutes and then a sample is removed and analyzed by infra-red spectroscopy.

Due to the thermal instability of the product, the progress of the reaction is followed by infra-red spectroscopy instead of vapor phase chromatography. There should be a reduction in the size of the carbonyl peak, from a 0–5% transmittance level to approximately 70–80%. A byproduct forms which has a carbonyl group absorbance at a slightly lower frequency than the starting material; 1778 cm$^{-1}$ vs 1786 cm$^{-1}$, respectively. There should be a new small peak observed at approximately 3050 cm$^{-1}$ which corresponds to the formation of the epoxide group in the desired product.

Once it has been determined that the reaction is complete, water (200 ml) is added to the reaction mixture through the additional funnel.

The reaction mixture is partitioned between ether (250 ml) and water. The organic phase is separated and the solvent in removed by rotoryevaporation. The aqueous phase is extracted with ether (3×100 ml) and the extracts are combined with the organic layer. The solvent volume is reduced by rotoevaporation and the residue is dried over anhydrous magnesium sulfate. The solid is filtered out and the remaining solvent removed under vacuum leaving a cloudy yellow oil, suitable for the next reaction.

The 4-(5-methoxyheptyl)spiro[bicyclo[3.2.0]heptane-6,2'-oxirane] thus obtained shows infrared maxima at 2931, 2855, 2817, 1463, 1383, 1379, 1195, 1156, 1094, and 920 cm$^{-1}$ (*Formula I*, $X=-(CH_2)_4-CH(OCH_3)-C_2H_5$).

This oxirane can also be prepared by using an equimolar amount of dimethylsulfonium methylide in place of the dimethyloxysulfonium methylide.

On standing at room temperature, e.g. for three days, the oxirane spontaneously rearranges to form the 4-(5-methoxyheptyl) bicyclo[3.3.0]octan-7-one, which can also be referred to as hexahydro-4-(5-methoxyheptyl)-2-(1H)-pentalenone (Formula II, $X=-(CH_2)_4-CH(OCH_3)-C_2H_5$).

EXAMPLE 3

Ring Expansion

To a 250 ml, 3-necked round bottomed flask equipped with a Friedrich condenser and magnetic stirrer are added (7.1 g, 0.028 moles) of 4-(5-methoxyheptyl)-spiro[3.2.0]heptane-6,2'-oxirane, in 50 ml dichloromethane, followed by a stoichiometric equivalent of lithium iodide trihydrate (3.77 g, 0.028 moles). The solution is stirred and heated under reflux in a 45° C. water bath for 60 minutes.

The reaction mixture is washed with a saturated solution of sodium chloride (2×100 ml). The organic phase is separated and dried over anhydrous magnesium sulfate. The solid is filtered out and the remaining solvent removed under vacuum leaving a cloudy yellow oil. The product is submitted to short path distillation under reduced pressure, leaving the crude product as a clear yellow oil.

The product is purified by high performance liquid chromatography (HPLC) with the Varex PSLC-100 chromatography system. The solvent system consists of a 13:1 hexane to ethyl acetate (v/v). The crude product (6.4 g) is manually injected into a 40 ml loop packed with glass beads. The sample is passed through a pre-column (6 cm×10 cm) and a stainless steel column (6 cm ×30 cm) packed with silica gel (32-63 mesh). The effluent is collected into 500 ml flasks and is monitored by an ultra-violet detector set at 286 nm. The purity of the collected fractions is determined by vapor phase chromatography. Only those fractions containing the desired product in a purity greater than 95% are combined and the solvent is removed by rotoevaporation. The residue is then distilled under reduced pressure yielding the purified product as a clear, colorless oil.

The 4-(5-methoxyheptyl)bicyclo[3.3.0]octan-7-one shows infrared maxima at 2928, 2853, 2828, 1740, 1460, 1402, 1735, 1158, 1122, 1093, 1050, 1035, 960 and 740 cm$^{-1}$.

EXAMPLE 4

4-(5-Ethoxyheptyl)spiro[bicyclo[3.2.0]heptane-6,2'oxirane]

To 400 g of 5-hydroxyheptanoic acid in a reaction vessel containing ethanol (4000 ml) and triethylorthoformate (4000 ml), perchloric acid (160 ml) is added slowly and the mixture is stirred at room temperature for 4 hours, after which time sodium hydroxide pellets (230 g) are added to stop the reaction. Once the perchloric acid has been neutralized the ethanol and triethylorthoformate are removed under vacuum. The residue is partitioned between ether (2000 ml) and water (1000 ml). The organic phase is separated and the aqueous layer extracted with ether (3×500 ml). The organic extracts are combined and dried over anhydrous sodium sulfate. The remaining solvent is removed under vacuum leaving a clear orange oil. The crude ethyl 5-ethoxyheptanoate is fractionally distilled under reduced pressure leaving a clear, colorless oil (302 g, 1.49 moles), BP 120° C./10 cm Hg.

Analysis: IR: 2971, 2933, 2874, 1736, 1461, 1448, 1418, 1400, 1372, 1348, 1300, 1241, 1196, 1177, 1106, 1076, 1035, 1014, 968, 921, 856, and 826 cm$^{-1}$.

A solution of tetrahydrofuran (2000 ml) and lithium aluminum hydride (46 g, 1.21 moles) is cooled in a −60° C. dry ice/ethanol bath. Ethyl 5-ethoxyheptanoate (302 g ,1.49 moles) is diluted in tetrahydrofuran (300 ml) and added dropwise to the stirring reaction. After the addition is complete the reaction is warmed to room temperature and stirred for an additional hour. The solution is cooled in a −78° C. dry ice/ethanol bath and the excess hydride is destroyed by adding dropwise the following: water (46 ml), 15% sodium hydroxide solution (46 ml), and water (136 ml). The reaction is filtered and the solids washed several times with tetrahydrofuran (3×500 ml). The volume of the filtrate is reduced under vacuum and the residue dried over anhydrous magnesium sulfate. The remaining solvent is then removed leaving a clear, colorless oil of 5-ethoxyheptanol suitably pure for the next reaction (238 g, 1.49 moles).

Analysis: IR: 3397 (broad), 2971, 2937, 2872, 1460, 1448, 1403, 1380, 1372, 1346, 1107, 1076, and 975 cm$^{-1}$.

5-Ethoxyheptanol (238 g, 1.49 moles) is diluted in pyridine (128 g, 1.62 moles). The solution is stirred at room temperature and thionyl chloride (388 g, 3.22 moles) is added dropwise over 2 hours, after which time the reaction is heated in a 70° C. water bath for 2 additional hours. Water (700 ml) is added to the reaction and the organic layer separated. The aqueous layer is extracted with hexane (3×400 ml) and the extracts combined with the organic phase. The organic phase is then washed with a 10% sodium hydroxide solution (1000 ml). The solvent volume is reduced under vacuum and the residue dried over anhydrous magnesium sulfate. The remaining solvent is removed leaving 1-chloro-5-ethoxyheptane as a clear light yellow oil. The crude product is fractionally distilled under reduced pressure leaving 1-chloro-5-ethoxyheptane as a clear, colorless oil (162 g, 1.13 moles), BP 96° C./9.5 cm Hg.

Analysis: IR: 2968, 2933, 2868, 1459, 1445, 1400, 1370, 1344, 1309, 1157, 1107, 1076, 994, 979, 734, and 649 cm$^{-1}$.

The next procedure followed is the same as that described in Example 1A and B substituting an equivalent amount of 1-chloro-5-ethoxyheptane dissolved in tetrahydrofuran. The crude product is distilled under reduced pressure leaving 3-(5-ethoxyheptyl)cyclopentene as a clear, colorless oil (121 g, 0.575 moles), BP 76° C./0.34 mm.

A solution containing trichloroacetyl chloride (187 g, 1.03 moles) and phosphorous oxychloride (158 g, 1.03 moles), both dissolved in 500 ml ether (1700 ml) is added dropwise to a reaction vessel containing zinc/copper couple (75 g, 1.15 moles), 3-(5-ethoxyheptyl)cyclopentene (170 g, 0.573 moles), and ether (1700 ml). After the addition is complete the reaction is refluxed for 4 hours. The reaction vessel is cooled to room temperature and the mixture neutralized by adding it to a saturated solution of sodium bicarbonate. The solution is filtered, the phases separated, and the aqueous layer is extracted with ether. The organic phases are combined and dried over anhydrous sodium sulfate. The solvent is removed under vacuum leaving a clear yellow oil. The crude product is fractionally distilled under vacuum leaving the product as a clear, colorless oil of 7,7-dichloro-4-(5-ethoxyheptyl)bicyclo [3.2.0]heptan 6-one, BP 145° C./0.3 mm.

Analysis: IR: 2965, 2931, 2862, 1803, 1480, 1461, 1450, 1400, 1370, 1345, 1225, 1107, 1080, 1028, 940, 822, 800, 738, 725, 670 and 654 cm$^{-1}$.

Dehalogenation by the process of Example 1C using zinc and acetic acid produces 4-(5-ethoxyheptyl)bicyclo[3.2.0]heptan-6-one. Reaction of 0.032 moles of this compound by the procedure of Example 2 with 0.034 moles of dimethylsulfonium methylide produces the 4-(5-ethoxyheptyl)spiro[bicyclo[3.2.0]heptane-6,2'-oxirane].

On standing or on reaction by the ring enlargement procedure of Example 3, there is obtained 4-(5-ethoxyheptyl)bicyclo[3.3.0] octan-7-one [4-(5-ethoxyheptyl) hexahydro-2(14)-pentalenone] as a clear, colorless oil.

Analysis: IR: 2959, 2929, 2859, 1740, 1461, 1404, 1370, 1346, 1157, 1109 and 1080 cm$^{-1}$.

EXAMPLE 5

(4-Heptyl)-spiro[bicyclo[3.2.0]heptane-6,2'-oxirane]

Under an inert atmosphere, 1-bromoheptane (100 g, 0.56 moles) in tetrahydrofuran (100 ml), is added portionwise to a refluxing solution of tetrahydrofuran (100 ml) and granular magnesium (25 g). After the addition is complete the reaction is refluxed an additional 2 hours and the resultant Grignard salt is cooled to room temperature, cannulated into a three liter flask, and cooled to −20° C. A 0.1M solution of Li$_2$CuCl$_4$ (1.7 mmoles) is added, followed by the dropwise addition of 3-chlorocyclopentene (57 g, 0.56 moles) cooled in a −20°

C. dry ice/ethanol bath. After the addition is complete the mixture is warmed to room temperature. Water (500 ml) is added. The reaction mixture is extracted with hexane (3×400 ml). The organic layers are combined, washed with brine (2×500 ml) and dried over anhydrous sodium sulfate. The remaining solvent is removed under vacuum leaving a clear yellow oil. The crude 3-heptylcyclopentene is fractionally distilled under reduced pressure leaving a clear, colorless oil, BP 41° C./0.35 mm.

The next procedure followed is that of the preceding Example for the preparation of 7,7-dichloro-4-(5-ethoxyheptyl)bicyclo [3.2.0] heptan-6-one, substituting 3-heptylcyclopentene (49 g, 0.30 moles) diluted in ether (490 ml), trichloroacetyl chloride (97 g, 0.53 moles) and phosphorous oxychloride (81 g, 0.53 moles) both diluted with ether (150 ml), zinc/copper couple (30 g, 0.59 moles) were used. The crude product is submitted to short path distillation and subsequently fractionally distilled under reduced pressure, leaving a clear, colorless oil of 7,7-dichloro-4-heptylbicyclo[3.2.0]heptan-6-one (20.6 g, 0.075 moles), BP 115° C./0.22 mm.

Analysis: IR: 2955, 2925, 2853, 1803, 1464, 1451, 1380, 1225, 1030, 965, 815, 790, 740, 725, and 670 cm$^{-1}$.

The product is dehalogenated as in Example 1C using zinc and acetic acid and the 4-heptylbicyclo[3.2.0]heptan-6-one is converted to the oxirane (Formula I, $X=-(CH_2)_6-CH_3$) by the process of Example 2 using dimethylsulfonium methylide at room temperature. By the process of Example 3 there is formed 4-heptylbicyclo[3.3.0]octan-7-one.

Chromatography on silica gel and short path vacuum distillation yields a clear, colorless oil.

Analysis: IR: 2949, 2922, 2852, 1740, 1465, 1404, 1375, 1239, and 1155 cm$^{-1}$.

EXAMPLE 6

4-[(2,2-dimethylethyl)dimethylsiloxy]pentyl-spiro[bicyclo[3.2.0]heptane-6,2'-oxirane]

A. 5-Chloropentanol (325 g, 2.65 moles) is added to a solution containing tert-butyldimethylsilyl chloride (439 g, 2.91 moles) and dimethylformamide (1.625 liters). The solution is stirred and imidazole (199 g, 2.91 moles) is added at once. The solution is stirred at room temperature for 6 hours, after which time water (1 liter) is added and the reaction is partitioned with hexanes. The organic phase is separated and the solvent volume reduced under vacuum. The residue is dried over anhydrous magnesium sulfate and the remaining solvent removed under vacuum, leaving a clear, colorless oil. The crude product is subsequently fractionally distilled under reduced pressure leaving the product as a clear, colorless oil (534 g, 2.26 moles), BP 71° C./0.3 mm.

Analysis: IR: 2958, 2930, 2898, 2862, 2802, 2739, 1472, 1463, 1447, 1434, 1407, 1389, 1361, 1353, 1291, 1257, 1218, 1153, 1106, 1055, 1031, 1024, 1007, 983, 939, 928, 913, 836, 813, 776, 727, 678, and 657 cm$^{-1}$.

B. Under an inert atmosphere, the material thus obtained, [(5-chloropentyl)oxy] (1,1-dimethylethyl)dimethylsilane (534 g, 2.26 moles), diluted in tetrahydrofuran (500 ml), is added portionwise to a refluxing solution of tetrahydrofuran and granular magnesium (75 g). After the addition is complete the reaction is refluxed two additional hours and the resultant Grignard salt is cooled to room temperature, cannulated into a three liter flask, and cooled to −20° C. A solution of Li$_2$CuCl$_4$ (6.4 mmoles) is added, followed by the dropwise addition of 3-chlorocyclopentene (219 g, 2.1 moles) cooled in a −20° C. dry ice/ethanol bath. After the addition is complete the mixture is warmed to room temperature. Water (500 ml) is added. The reaction mixture is extracted with hexane (3×400 ml). The organic layers are combined, washed with brine (2×500 ml) and dried over anhydrous sodium sulfate. The remaining solvent is removed under vacuum leaving a clear yellow oil. The crude product is fractionally distilled under reduced pressure leaving a clear, colorless oil (478 g, 1.78 moles), BP 96° C./0.3 mm.

Analysis: IR: 3049, 2948, 2928, 2854, 1469, 1460, 1387, 1359, 1254, 1103, 1052, 1027, 1005, 938, 834, 811, 773, 715, 676, and 661 cm$^{-1}$.

C. A solution containing trichloroacetyl chloride (149 g, 0.82) and phosphorous oxychloride (126 g, 0.82 mole) dissolved in ether (600 ml) is added dropwise to a reaction vessel containing 3-(5-[(1,1-dimethylethyl)-dimethylsiloxy]pentyl)cyclopentene, the product thus obtained, (200 g, 0.745 moles), zinc (54 g, 0.82 moles) and ether (2 liters). After the addition is complete the reaction is refluxed for 4 hours. The reaction vessel is cooled to room temperature and the mixture neutralized by adding it to a saturated solution of sodium bicarbonate. The solution is filtered, the phases separated, and the aqueous layer is extracted with ether (2×1000 ml). The organic phases are combined and dried over anhydrous sodium sulfate. The solvent is removed under vacuum leaving a clear yellow oil. The crude product is kugelrohred and then fractionally distilled under vacuum leaving the product as a clear, colorless oil (148 g, 0.392 moles), BP 178° C./0.25 mm.

Analysis: IR: 2950, 2929, 2897, 2855, 1804, 1460, 1447, 1405, 1386, 1359, 1301, 1271, 1254, 1223, 1185, 1157, 1100, 1057, 1029, 1005, 974, 962, 937, 923, 901, 835, 813, 774, 741, and 673 cm$^{-1}$.

The resulting 7,7-dichloro-4-[5-[(1,1-dimethylethyl)-dimethylsilyl]oxypentyl]bicyclo[3.2.0]heptan-6-one is dechlorinated by the procedure of Example 1C using zinc and acetic acid and the product treated with dimethylsulfonium methylide as in Example 2 to produce 4-([2,2-dimethylethyl)dimethylsilyl]oxypentyl spiro[-bicyclo [3.2.0]heptane-6,2'- oxirane] (Formula I, $X=-(CH_2)_4-CH_2O-Si(CH_3)_2-C(CH_3)_3$).

Ring enlargement by standing or reaction of Example 3 yields 4-(5-[1,1-dimethylethyl)dimethylsiloxy]pentyl)-bicyclo[3.3.0]octan-7-one.

The 4-(5-hydroxypentyl)bicyclo[3.3.0]octan-7-one, obtained therefrom by the process of Example 7A using hydrofluoric acid, is a colorless oil.

Analysis: IR: 3441, 2925, 2854, 1736, 1460, 1402, 1255, 1162, 1085, and 1065 cm$^{-1}$.

EXAMPLE 7

4-[5-(1,1-Dimethylethyl)dimethylsiloxy]heptyl[-spiro[3.2.0]heptane-6,2'-oxirane]

A. 3-(5-[(1,1-Dimethylethyl)dimethylsiloxy]pentyl)-cyclopentene (300 g, 1.170 moles) is diluted with acetonitrile (3000 ml) and a 40% stock solution of hydrofluoric acid (166 ml) is added. The reaction is stirred at room temperature for 10 minutes and then slowly neutralized with a saturated solution of sodium bicarbonate. The reaction is partitioned between ether (1500 ml) and the aqueous phase extracted with ether (1×1000 ml). The organic layers are combined and the solvent volume is reduced under vacuum. The residue is dried over anhydrous sodium sulfate and the remaining solvent removed leaving a clear, colorless oil. The product is distilled under vacuum leaving a product sufficiently pure for the next reaction (171 g, 1.11 moles).

Analysis: IR: 3382 (broad), 3052, 2934, 2856, 1462, 1440, 1373, 1057, 1016, 717, 673, 663 cm$^{-1}$.

B. Pyridinium dichromate (621 g, 1.65 moles) is added to a solution of 2-cyclopentene-1-pentanol thus obtained (170 g, 1.10 moles) dissolved in methylene chloride (1552 ml). The solution is stirred at room temperature for 12 hours after which time isopropanol is added and the reaction stirred for 1 hour. The reaction is filtered through a pad of activated magnesium silicate (Florisil) and the solid rinsed with several portions of methylene chloride (3×400 ml). The solvent is removed under vacuum leaving a clear yellow oil. The crude product is kugelrohred under vacuum leaving clear, colorless oil (63 g, 0.414 moles).

Analysis: IR: 3052, 2934, 2854, 2719, 1731, 1462, 1442, 1411, 1392, 1361, 1285, 1260, 1178, 1166, 1150, 1091, 1055, 1034, 1007, 912, 719, and 612 cm$^{-1}$.

In an inert atmosphere the material thus obtained, 2-cyclopentene-1-pentanal (75 g, 0.493 moles), is dissolved in anhydrous tetrahydrofuran (750 ml) and cooled in a −30° C. ethanol/dry ice bath. Ethyl magnesium bromide (0.493 moles) is added dropwise to the stirring reaction mixture for a period of over 2 hours. The reaction is warmed to 0° C. and water (100 ml), followed by 15% sulfuric acid (200 ml), is added. The aqueous layer is extracted with ether (2×300 ml) and the organic extracts are combined, reduced in volume and washed with brine (400 ml). The alpha-ethyl-2-cyclopenten-1-pentanol is dried over anhydrous sodium sulfate and the remaining solvent removed under vacuum leaving a clear yellow oil. The crude product is chromatographed on silica gel and subsequently distilled under vacuum leaving clear, colorless oil (10.2 g, 0.056 moles).

Analysis: IR: 3387 (broad), 3054, 2930, 2875, 2857, 1463, 1441, 1432, 1422, 1413, 1378, 1360, 1331, 1314, 1284, 1262, 1250, 1147, 1118, 1064, 1054, 1037, 1025, 989, 970, 913, 717, 678 and 658 cm$^{-1}$.

C. 3-(5-[(1,1-Dimethylethyl)dimethylsiloxy]heptyl)-cyclopentene is obtained by the procedure followed is that described in the Example 6A using alpha-ethyl-2-cyclopenten-1-pentanol (32.5 g, 0.177 moles), t-butyl-dimethylsilylchloride (29.3 g, 0.194 moles), imidazole (13.3 g, 0.194 moles), and dimethylformamide (163 ml). The crude product is fractionally distilled under reduced pressure leaving a clear, colorless oil (48 g, 0.162 moles), BP 103° C./0.15 mm.

Analysis: IR: 3046, 2925, 2850, 1460, 1445, 1404, 1374, 1358, 1252, 1214, 1183, 1127, 1108, 1064, 1055, 1005, 936, 909, 893, 857, 833, 812, 789, 771, 714, and 658 cm$_{-1}$.

D. 7,7-Dichloro-4-[5-[(1,1-dimethylethyl)dimethylsilyl]oxy]bicyclo[3.2.0]heptan-6-one is obtained by the procedure of Example 6C substituting 3-(5-[(1,1-dimethylethyl)dimethylsiloxy]hept-1-yl)cyclopentene (or [[5-(2-cyclopenten-1-yl)-1-ethylpentyl]oxy]1,1-dimethylethyl)dimethylsilane) (0.162 moles, 48.0 g), trichloroacetyl chloride (0.324 moles, 59 g, 36.2 ml), and phosphorous oxychloride (0.324 moles, 50 g, 30.2 ml). The crude product is subjected to short path vacuum distillation and then fractionally distilled under reduced pressure leaving a clear, colorless oil (36 g, 0.088 moles), BP 168° C./0.3 mm.

Analysis: IR: 2827, 2876, 2852, 1802, 1460, 1405, 1376, 1359, 1306, 1252, 1223, 1182, 1158, 1129, 1109, 1066, 1029, 1012, 966, 936, 896, 859, 833, 789, 771, 740, 672, 622, and 619 cm$^{-1}$.

This oily product is dechlorinated by the process of Example 1 using zinc and acetic acid. The resulting product is converted by the process of Example 2 to 4-[5-(1,1-dimethylethyl)dimethylsiloxy]heptyl[-spiro[3.2.0]heptane-6,2'-oxirane] of the formula

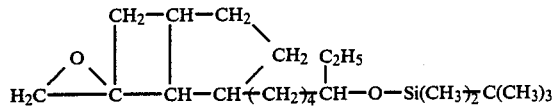

On standing or treatment by the procedure of Example 3, ring enlargement occurs. Acid treatment with hydrofluoric acid of the silyl ether group, as earlier in this Example, yields a yellow oil.

Chromatography on silica gel leaves pure 4-(5-hydroxyhept-1yl)bicyclo[3.3.0]octan-7-one, or hexahydro-4-(5-hydroxyheptyl)2(1H)-pentalenone.

Analysis: IR: 3395, 2935, 2855, 1748, 1465, 1267, 1245, 1160, 1120, 965, 920, 810, 785, and 745 cm$^{-1}$.

EXAMPLE 8

4-[3-(1,1-Dimethylethyl)dimethylsiloxypentyl]-spiro[3.2.0]heptane6,2'-oxirane

1-Chloro-3-pentanol is prepared by reducing 1-chloro-3-pentanone (100 g, 0.83 moles) is dissolved in 95% ethanol (100 ml) using sodium borohydride (8.6 g, 0.23 moles) dissolved in 95% ethanol (200 ml). The product is fractionally distilled under reduced pressure leaving a clear, colorless oil (50 g, 0.41 moles), BP 40° C./1.4 mm.

Analysis: IR: 3348 (broad), 2969, 2934, 2874, 1462, 1454, 1446, 1413, 1377, 1344, 1309, 1299, 1210, 1172, 1128, 1094, 1079, 1060, 1051, 1022, 1013, 997, 980, 951, 862, 721, and 649 cm$^{-1}$.

Using the procedure of Example 6A substituting 1-chloro-3-pentanol (50 g, 0.41 moles), tert-butyldimethylsilyl chloride (71, 0.47 moles), imidazole (32.6 g, 0.48 moles), and dimethylformamide (150 ml), there is obtained (3-chloro-1-ethylpropoxy)(1,1-dimethylethyl)-dimethylsilane. The crude product is fractionally distilled under vacuum leaving a clear, colorless oil (78 g, 0.33 moles), BP 48° C./0.1 mm.

Analysis: IR: 2958, 2933, 2892, 2887, 2859, 2826, 2803, 1472, 1463, 1447, 1468, 1389, 1374, 1361, 1337, 1310, 1293, 1280, 1257, 1212, 1185, 1175, 1168, 1135, 1088, 1043, 1032, 1006, 958, 939, 913, 901, 837, 809, 775, 730, 712, 676, and 654 cm$^{-1}$.

Further following the procedure described in Example 6B, substituting 3-chloro-1-ethylpropoxy(1,1-dimethylethyl)dimethylsilane (78 g, 0.33 moles) diluted in tetrahydrofuran (100 ml), granular magnesium (24 g, 1.00 moles), tetrahydrofuran (100 ml), 0.1M solution of Li$_2$CuCl$_4$ (1.0 mmole), and 3-chlorocyclopentene (33 g, 0.33 moles) dissolved in tetrahydrofuran (50 ml), one obtains [3-(2-cyclopenten-1-yl)-1-ethylpropoxy](1,1-dimethylethyl)dimethylsilane. The crude product is distilled under reduced pressure leaving a clear yellow oil (21 g, 0.078 moles), BP 69° C./0.1 mm.

Analysis: IR: 3055, 2956, 2933, 2902, 2858, 1472, 1463, 1374, 1361, 1256, 1136, 1097, 1060, 1035, 1006, 835, 806, 774, 717, and 661 cm$^{-1}$.

In the next step, the procedure of Example 6C is used, but there are substituted: 3-(3-[(1,1-dimethylethyl)dimethylsiloxy]pent-1-yl)cyclopentene ([3-(2-cyclopenten-1-yl)-1-ethylpropoxy](1,1-dimethylethyl)dimethylsilane) (15 g, 0.056 moles) dissolved in ether (100 ml), trichloroacetyl chloride (20.3 g, 0.11 moles) and phosphorous oxychloride (17.2 g, 0.11 moles) both dissolved in ether (50 ml), zinc/copper couple (10 g, 0.16 moles). The crude product is subjected to short path vacuum distillation leaving a clear yellow oil (13.5 g, 0.035 moles) of 7,7-dichloro-4-[3-[[1,1-dimethylethyl)dimethylsilyloxy]pentyl]bicyclo[3.2.0]heptan-6-one.

Analysis: IR: 2958, 2932, 2903, 2858, 1806, 1471, 1463, 1449, 1374, 1361, 1256, 1184, 1135, 1099, 1065, 1052, 1031, 1006, 966, 960, 939, 898, 835, 808, 774, 740, and 674 cm$^{-1}$.

The product is dechlorinated by the process of Example 1C using zinc and acetic acid.

4-[3-(1,1-Dimethylethyl)dimethylsiloxypentyl]-spiro[3.2.0]heptane-6,2'-oxirane is prepared by the process of Example 2 (Formula I, X= —(CH$_2$)$_2$—CH(C$_2$H$_5$)—O—Si(CH$_3$)$_2$—C(CH$_3$)$_3$). Conversion to the octan-7-one is carried out by the process of Example 3. The siloxy group is removed by treatment with glacial acetic acid to yield 4-(3-hydroxpentyl)bicyclo[3.3.0]octan-7-one. The crude product is chromatographed on silica gel and subsequently subjected to short path distillation under vacuum leaving a clear, colorless oil (1.0 g, 4.8 mmoles).

Analysis: IR: 3411, 2961, 1739, 1451, 1406, 1364, 1258, 1162, 1115, 1110, 1071, 1063, 1115, 1096, 1037, 1027, 917, 864, 809, 798, 736, 702, 689, 681, and 657 cm$^{-1}$.

EXAMPLE 9

4-(5-Acetoxypentyl)spiro[bicyclo[3.2.0]heptane-6,2'-oxirane]

A. 7,7-Dichloro-4-[5[(1,1-dimethylethyl)dimethylsilyl]oxy]pentyl]bicyclo [3.2.0]heptan-6-one (Example B, 321 g, 0.084 moles) is diluted with acetonitrile (161 ml) and a 40% stock solution of hydrofluoric acid (8 ml) is added. The reaction is stirred at room temperature for 10 minutes and then slowly neutralized with a saturated solution of sodium bicarbonate. The reaction mixture is partitioned with ether and the aqueous phase extracted with ether. The organic layers are combined and the solvent volume is reduced under vacuum. The residue is dried over anhydrous sodium sulfate and the remaining solvent removed leaving a clear, colorless oil. The product is subjected to silica gel chromatography and then short path distillation under vacuum, leaving 7,7-dichloro-4-(5-hydroxypent-1-yl)bicyclo[3.2.0]heptan-6-one, leaving a clear colorless oil.

Analysis: IR: 3406 (broad), 2931, 2856, 1801, 1460, 1372, 1348, 1334, 1318, 1302, 1276, 1223, 1159, 1131, 1073, 1055, 1028, 992, 987, 970, 959, 915, 817, 739, and 623 cm$^{-1}$.

B. This oily product (7 g, 26 mmoles) is dissolved in glacial acetic acid (49 ml) and zinc powder (14 g) is added. The reaction is then heated in a 70° C. water bath and stirred for 4 hours. The reaction is cooled to room temperature and partitioned between ether (250 ml) and water (250 ml). The aqueous phase is extracted with ether (2×200 ml), the extracts are combined and then neutralized with a solution of saturated bicarbonate. The ether layer is dried over anhydrous sodium sulfate and the solvent removed under vacuum leaving a clear, colorless oil. The crude product is chromatographed on silica gel and subsequently subjected to short path distillation under vacuum leaving 4-(5-acetoxypentyl)bicyclo[3.2.0]heptan-6-one as a clear, colorless oil.

Analysis: IR: 2934, 2857, 1778, 1737, 1462, 1387, 1365, 1297, 1239, 1138, 1117, 1089, 1042, 973, and 705 cm$^{-1}$.

C. Reaction by the procedure of Example 2 yields the 4-(5-acetoxypentyl)spiro[bicyclo[3.2.0]heptane-6,2'-oxirane] (Formula I, X=—(CH$_2$)$_5$—OC)—CH$_3$), which, on reaction by the procedure of Example 3, rearranges to 4-(5-acetoxypentyl)bicyclo [3.2.0]octan-7-one.

Analysis: IR: 2932, 2856, 1739, 1462, 1404, 1385, 1365, 1239, 1160, and 1044 cm$^{-1}$.

EXAMPLE 10

4-(5-Acetoxyheptyl)spiro[bicyclo[3.2.0]heptane-6,2'oxirane

4-[5-[(1,1-Dimethylethyl)dimethylsilyl]oxy]pentyl]-bicyclo [3.2.0]heptan-6-one (Example 6C) is converted to the 5-hydroxypentyl compound by cleavage with hydrofluoric acid.

The resulting 4-(5-hydroxyheptyl)bicyclo[3.2.0]heptan-6-one (0.85 g, 3.8 mmoles) is diluted with glacial acetic acid (7 ml). The mixture is stirred and heated in a 75° C. oil bath for 24 hours, after which time water (20 ml) is added and the reaction mixture is partitioned between ether. The ether layer is separated and the aqueous phase extracted again with ether (2×50 ml). The extracts and the organic phase are combined and neutralized with saturated sodium bicarbonate. The organic phase is dried over anhydrous magnesium sulfate and the remained solvent removed under vacuum leaving a pale yellow oil. The product is subjected to short path vacuum distillation and yields a clear oil.

The 4-(5-acetoxyheptyl)bicyclo[3.2.0]heptan-6-one thus obtained is treated with dimethylsulfonium methylide to yield the 4-(5-acetoxyheptyl)bicyclo[3.2.0]heptane-6,2'-oxirane (Formula I, X=—(CH$_2$)$_4$—CH(C$_2$H$_5$)—(O—CO—CH$_3$), which is converted by the method of Example 3 to 4-(5-acetoxyheptyl)bicyclo[3.3.0]octan-7-one (4-[5-(acetyloxy)pentyl]-hexahydro-2(1H)-pentalenone). Chromatography on silica gel and subsequent short path distillation under vacuum yields a clear, colorless oil.

Analysis: IR: 2930, 2855, 1738, 1460, 1403, 1371, 1245, 1160, 1117, 1019, and 958 cm$^{-1}$.

EXAMPLE 11

4-(4-Carbomethoxybutyl)spiro[bicyclo[3.2.0]heptane-6,2'-oxirane]

7,7-Dichloro-4-[5-[(1,1-dimethylethyl)dimethylsilyl)oxy]pentyl]bicyclo[3.2.0]heptan-6-one (Example 6C) is dehalogenated with zinc and acetic acid by the process of Example 1C and the siloxy group is removed using hydrofluoric acid as shown in Example 7A.

4-(5-Hydroxypentyl)bicyclo[3.2.0]heptan-6-one thus obtained (0.47 g, 2.4 mmoles) is mixed with a 10% solution of sodium carbonate (0.51 ml). The reaction mixture is cooled in an ice bath and a solution of potassium permanganate (0.48 g dissolved in 12 ml water) is slowly added over 10 minutes. The ice bath is then removed and the reaction mixture stirred at room temperature for 12 hours, after which time the precipitated manganese dioxide is filtered off and the filtrate extracted with ether. The solution is acidified with dilute sulfuric acid and the organic layer separated. The aqueous phase is extracted with ether and the ether extracts are combined and dried over anhydrous sodium sulfate. The solvent is removed under vacuum leaving a clear colorless oil. The crude product is chromatographed on silica gel and subsequently subjected to short path distillation under reduced pressure leaving a clear, colorless oil (0.050 g, 0.22 mmoles).

The product thus prepared, 4-(5-carboxybutyl)bicyclo[3.2.0]heptan-6-one (0.94 g, 4.4 mmoles), is diluted in absolute methanol (20 ml). The solution is stirred and concentrated sulfuric acid (0.5 g) is added. The solution is stirred under reflux for 4 hours, after which time the reaction mixture is partitioned between the organic phase (25 ml) and aqueous phase (50 ml). The organic phase is separated and the aqueous phase extracted with ether. The organic solutions are combined and dried over anhydrous magnesium sulfate. The solid is filtered off and the solvent removed under vacuum leaving an oil. The product is chromatographed on silica gel and subjected to short path distillation under reduced pressure, leaving the methyl ester as a clear, colorless oil.

Reaction with dimethylsulfonium methylide by the process of Example 2 yields 4-(4-carbomethoxybutyl)-spiro[bicyclo[3.2.0]heptane-6,2'-oxirane of the formula

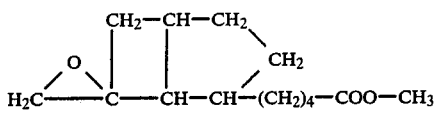

Treatment by the method of Example 3 yields 4-(4-carboxybutyl)bicyclo[3.3.0]octan-7-one methyl ester (methyl octahydro-5-oxo-1-pentalene pentanoate) which, after silica gel chromatography and vacuum distillation, forms a clear, colorless oil.

Analysis: IR: 2934, 2856, 1739, 1725, 1462, 1404, 1385, 1365, 1239, 1165, and 1044 cm$^{-1}$.

EXAMPLE 12

Ketols of 4-(5-oxoheptyl)spiro[bicyclo[3.2.0]heptane-6,2'-oxirane]

Acetals and ketals wherein the X group in Formula I is substituted by $(C^{1-6}\text{-alkylO})_2$ or $-O-(C^{1-6}\text{-alkylene})-O$-groups, are made by the usual techniques. For ketals the 1,2-ethyleneglycol or 1,3-propyleneglycol derivatives are conveniently used, e.g. for the preparation of the ketals of 4(5-oxoheptyl)bicyclo[3.2.0]heptan-6-one. This ketal is treated with dimethylsulfonium methylide by the method of Example 2 to yield the ethylene or propylene ketal of 4-(5-oxoheptyl)spiro[bicyclo[3.2.0]heptane6,2'-oxirane]. Reaction with lithium iodide by the method of Example 3 and acid hydrolysis of the ketal group yields 4-(5-oxoheptyl)bicyclo[3.3.0]octan-7-one. Silica gel chromatography and short path vacuum distillation produces a clear, colorless oil.

Analysis: IR: 2939, 2860, 1740, 1714, 1461, 1451, 1406, 1376, 1243, 1209, 1161, and 1112 cm$^{-1}$.

What is claimed is:

1. A compound of the formula

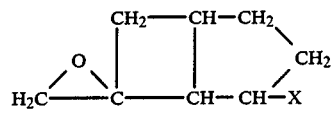

wherein X is a $C^{2-11}$-alkyl group substituted by a protected hydroxy, protected oxo or protected carboxy group.

2. A compound of claim 1 wherein the protected hydroxy is $C^{1-4}$ alkoxy.

3. A compound of claim 2 wherein the $C^{1-4}$-alkoxy group is methoxy.

4. A compound of claim 2 wherein the $C^{1-4}$-alkoxy group is ethoxy.

5. A compound of claim 1 wherein X is 5-methoxyheptyl.

6. A compound of claim 1 wherein X is 5-ethoxyheptyl.

7. A compound of claim 1 wherein X is a hydroxyheptyl group wherein the hydroxy group is protected by a tri($C^{1-5}$alkyl)silane group.

8. A compound of claim 1 wherein X is a $C^{2-9}$-alkyl group substituted by an $-O-Si(CH_3)_2-C(CH_3)_3$ group.

9. A compound of claim 1 wherein X is a

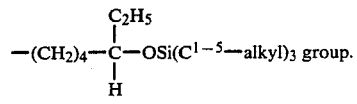

* * * * *